US00PP18952P2

(12) United States Plant Patent
Kordes

(10) Patent No.: US PP18,952 P2
(45) Date of Patent: Jun. 17, 2008

(54) CLIMBING ROSE PLANT NAMED 'KORCENTEX'

(50) Latin Name: *Rosa hybrida*
Varietal Denomination: KORcentex

(75) Inventor: Tim-Hermann Kordes, Offenseth-Sparrieshoop (DE)

(73) Assignee: W. Kordes' Söhne Rosenschulen GmbH & Co. KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/490,581

(22) Filed: Jul. 21, 2006

(51) Int. Cl.
*A01H 5/00* (2006.01)

(52) U.S. Cl. ..... Plt./114

(58) Field of Classification Search ..... Plt./114
See application file for complete search history.

(56) References Cited

PUBLICATIONS

QZ (CPVO) Application, 2005/0995, Jun. 1, 2005, W. Kordes Sohne.

*Primary Examiner*—Anne Marie Grunberg
*Assistant Examiner*—Louanne Krawczewicz Myers

(57) ABSTRACT

A new and distinct variety of rose with long lasting, novel pink flowers, and attractive foliage with good disease resistance. It exhibits uniform climbing growth with abundant flowers. The new variety propagates well from cuttings and by grafting. This new and distinct variety has shown to be uniform and stable in the resulting generations from asexual propagation.

2 Drawing Sheets

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORcentex'.

BACKGROUND OF THE INVENTION

The new variety of rose plant of the present invention originated from a controlled crossing in a breeding program of two distinct parents during the summer of 1997. The crossing was between an un-named seedling and 'Centenaire de Lourdes', a non patented rose.

The resulting seeds were planted in seedling beds during the following winter. The resulting seedlings were subsequently evaluated and exhibited distinctive physical and biological characteristics. The new rose plant was selected as a single plant due to its superior characteristics and asexually propagated from further evaluation. This new and distinctive rose variety is named 'KORcentex'.

SUMMARY OF THE INVENTION

The new rose plant may be distinguished from its seed parent, an un-named seedling, by the following combination of characteristics:

1. 'KORcentex' has pink flowers and the seedling parent has carmine red flowers; and
2. 'KORcentex' has flower blooms to 60 mm in diameter while the seed parent's blooms are 30 mm in diameter.

The new rose plant may be distinguished from its pollen parent, 'Centenarie de Loudes', by the following combination of characteristics:

1. 'KORcentex' has 6 double flowers in large clusters while the pollen parent has semi-double flowers in small clusters; and
2. 'KORcentex' is a very vigorous grower while the pollen parent is moderately vigorous.

The objective of the hybridization was to create a new and distinct rose plant with unique qualities, such as:

1. Upright, vigorous, and uniform growth and flowering;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORcentex' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORcentex' was selected in May, 1997 from the seedling beds to be asexually propagated for further evaluation. The first asexual propagation of 'KORcentex' was done by budding to seedling understocks in August, 1997 at the hybridizer's nursery in Offenseth-Sparrieshoop, Germany.

This initial and other subsequent propagations conducted in controlled environments show that the foregoing and all other characteristics of 'KORcentex' come true to form and are transmitted through succeeding generations. The new variety reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORcentex'. Specifically illustrated in SHEET ONE.

DETAILED BOTANICAL DESCRIPTION

Figures 1, 2, 3, 4, 5:
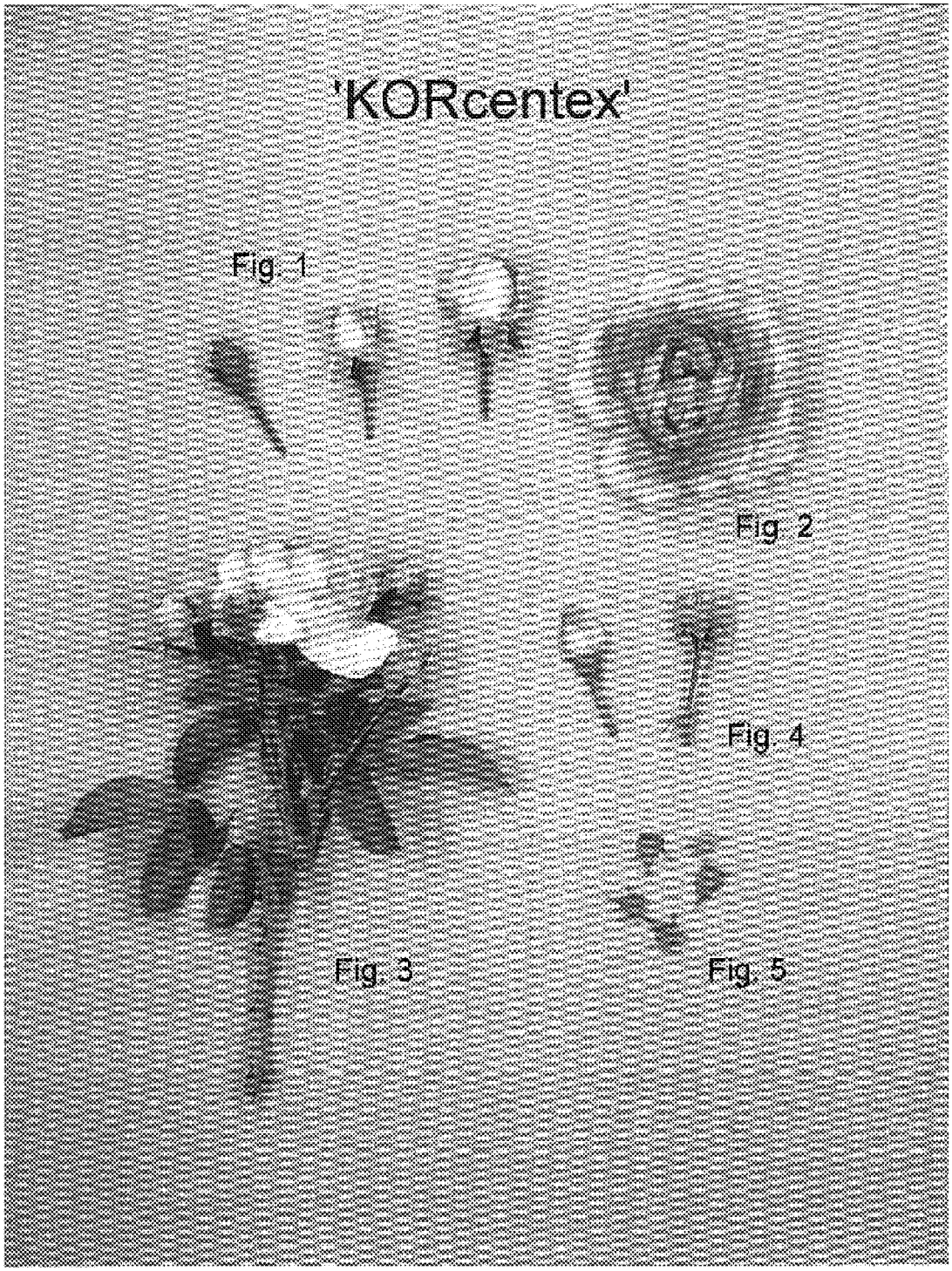
FIG. 1: Tight flower bud, and partially opened flower blooms.
FIG. 2: an open flower bloom.
FIG. 3: a flowering stem.
FIG. 4: a flower receptacle and base with and without petals removed.
FIG. 5: Sepals. Specifically illustrated in SHEET TWO.
Figures 6, 7, 8:
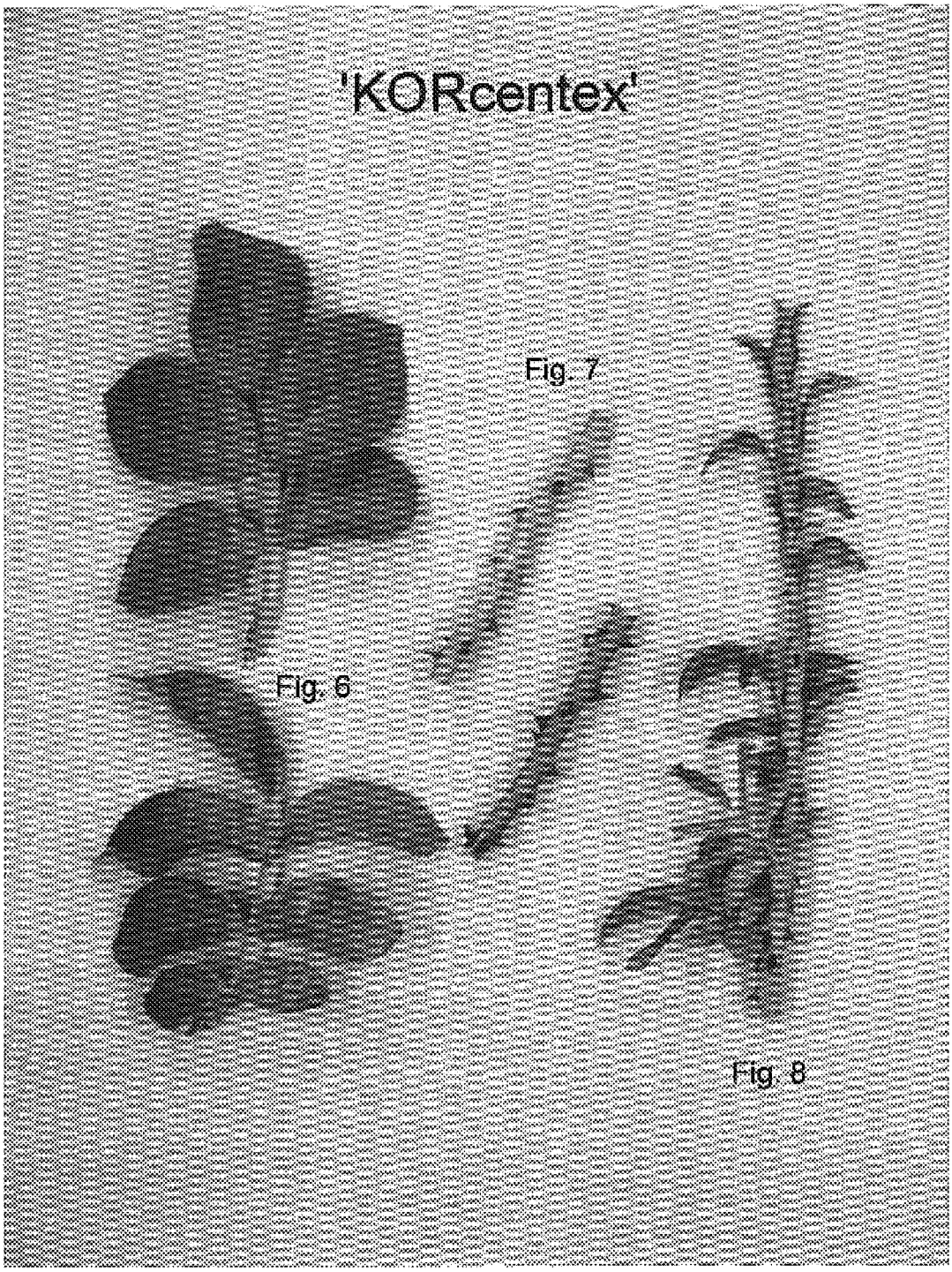
FIG. 6: Two leaves.
FIG. 7: a selection of a younger stem and mature stem exhibiting thorns.
FIG. 8: the juvenile foliage and stem material from the distal end of a stem.

The following is a description of 'KORcentex', as observed growing in a nursery in Jackson County, Oreg. on plants of three years of age. Color references are made using the Royal Horticultural Society (London, England) Colour Chart, 2001 except where common terms of color are used.

For a comparison, several physical characteristics of the rose variety 'KORadigel', a climbing rose variety from the same inventor described and illustrated in U.S. Plant Pat. No. 16,936 and issued on Aug. 1, 2006 are compared to 'KORcentex' in Chart 1.

CHART 1

| Characteristic | 'KORcentex' | 'KORadigel' |
|---|---|---|
| Bud color | Blend of Red-Purple Group 65D to Red-Purple Group 65A | Red-Purple Group 58A. |
| Flower color, general tonality | Red-Purple Group 58B to 58C. | Red-Purple Group N66B. |
| Stamens | Average 30 in number. | Approximately 40. |

Parents:

*Seed parent.*—'Un-named seedling'.

*Pollen parent.*—'Centenaire de Lourdes'.

Classification:

*Botanical classification.*—*Rosa hybrida* 'KORcentex'.

*Commercial classification.*—Climbing rose.

FLOWER AND FLOWER BUD

Blooming habit: Recurrent.

Flower bud:

*Size.*—Upon opening, 25–32 mm in length from base of receptacle to end of bud. Average bud diameter is 11–12 mm.

*Bud form.*—Globular.

*Bud and flower color.*—As sepals first unfold, bud color is a blend of Red-Purple Group 65D to Red-Purple Group 65A. When ¼ open, the color of the upper surface of petals transitions from Red-Purple Group 68B on the marginal zone to Red-Purple Group 69C on the basal zone. On the outer petal surface, the color of the marginal zone of petals transitions from Red-Purple Group 68B on the upper margin to Red-Purple Group 69C on the basal zone.

*Sepals.*—Size: Average 12–15 mm long×7–10 mm wide. Shape: Weak foliaceous appendages on three of the five sepals. Sepal apex is cirrose. Base is flat at union with receptacle. Quantity: Five. Surface texture: Inner side: Covered in fine hairs. Outer surface: Nearly smooth. Margins: With limited numbers of stipitate glands on the margins. Color: Upper surface Green Group 138A. Lower surface Green Group 143A. Some anthocyanin intonations on margins and outer lower sepal surface of Greyed-Red Group 182B.

*Receptacle.*—Surface: Smooth. Color: Green Group 138A. Shape: Broad funnel. Size: 8 mm (h)×8 mm (w).

*Peduncle.*—Surface: Nearly smooth, with limited numbers of fine hairs. Length: 25 to 50 mm average length. Diameter: 1.5 to 2.0 mm average diameter. Color: Green Group 138A. Most with some intonations of Greyed-Red Group 178B. Strength: Upright to nodding. Borne: Multiple flower buds per stem, ranging from 8 to 24.

Flower bloom:

*Fragrance.*—Moderate. Fresh floral scent.

*Duration.*—On the plant 4–6 days. Senesced petals drop away cleanly.

*Size.*—Average flower diameter is 60 mm when open. Average flower depth is 35 mm.

*Form.*—Nostaglic, resembles a quartered rosette. Shape of lower when viewed from the side: Upon open, upper part: Flattened convex. Upon opening, lower part: Convex. Open flower, upper part: Flattened convex. Open flower, lower part: Flat to flattened convex.

Color:

*Upon opening, petals.*—Outermost petals: Outer Side: Middle zone Red-Purple Group 69C. Marginal zone Red-Purple Group 73C. Inner Side: Middle zone Red-Purple Group 73C. Marginal zone Red-Purple Group 63C. Innermost petals: Outer Side: Color variable. Red-Purple Group 63B to Red-Purple Group 64C. Inner Side: Red-Purple Group 64C.

*Upon opening, basal petal spots.*—Basal area of coloration is relatively large, approx. 15–20% of the length of petal. Basal petal spot, outermost petals: Outer Side: Green-Yellow Group 1D. Inner Side: Green-Yellow Group 1D. Basal petal spot, innermost petals: Outer Side: Yellow-Orange Group 15B. Inner Side: Yellow Group 13C.

*After opening, petals.*—Outermost petals: Outer Side: Marginal zone Red-Purple Group 65A. Middle zone Red-Purple Group 65D. Inner Side: Marginal zone Red-Purple Group 67B and 67C. Middle zone Red-Purple Group 67C. Innermost petals: Outer Side: Marginal zone Red-Purple Group 73B. Middle zone Red-Purple Group 73D. Inner Side: Red-Purple Group 70C.

*After opening, basal petals spots.*—Basal petal spots, outermost petals: Outer Side: Green-Yellow Group 1D. Inner Side: Green-Yellow Group 1D. Basal petal spots, innermost petals: Outer Side: Yellow-Orange Group 15C. Inner Side: Yellow-Orange Group 15C. Variegations: Occasional streak in the petals of White Group 155A.

General tonality: On open flower, Red-Purple Group 58C to 58D. No change in the general tonality at the end of the third day. Afterwards, general tonality is Red-Purple Group 68B to 68C.

Petals:

*Petal count.*—Approximately 70–75 petals under normal conditions.

*Petal reflex.*—Petals reflex slightly.

*Petal edge.*—Nearly entire. Typically with an indentation at the center of the petals apex.

*Petal shape.*—Deltoid. Apex shape is round. Shape of base is acute.

*Petal size.*—35 mm long; 20 mm wide.

*Thickness.*—Average.

*Petal arrangement.*—Informal. Many petals overlapping and exhibiting some quartering.

*Petaloids.*—Present. Average of 10–15 per flower. Petaloids are 15 mm long and 6–10 mm wide. Color of inner side is Red-Purple Group 67B. Color of outer side is Red-Purple Group 67B. Surface texture is generally smooth, with some petals folded. Shape is ovate. Apex shape is rounded with undulations. Base is acute. Margins with undulations.

Reproductive organs:

*Pistils.*—Average number. Clustered at center. Approximately 20–30 present. Stigmas: Location: Superior in location to anthers. Color: Green-Yellow Group 146C. Styles: Length: 10 mm long. Color: Yellow-Green Group 146D.

*Stamens.*—Average 30 in number. Anthers: A number of the filaments lack anthers. Size: 1.0–1.5 mm long. Color: Yellow-Orange Group 15B. Pollen: Absent. Filaments: Color: Yellow-Orange Group 15B. Length: 6–10 mm. Variable.

THE PLANT

Plant growth: Vigorous growth with abundant bloom. Upright climbing habit. When grown as a budded nursery plant, after two years the average plant height is 200 cm and the average plant width is 100 cm.

*Stems.*—Stem color: Some areas of intonation of Greyed-Purple Group 183D. Young wood: Yellow-Green Group 146C. Older wood: Yellow-Green Group 146A. Stem surface: Young wood: Smooth. Older wood: Smooth.

*Prickles.*—Present. Incidence: 12 per 10 cm of stem. Size: Average length: 6–7 mm. Color: Immature prickles: Greyed-Red Group 179A. Mature prickles: Greyed-Purple Group 183A. Shape: Concave to slightly downward hooked.

*Leaves and leaflets.*—Normally 7 leaflets on normal leaves in middle of the stem. Leaf size: 100 mm (l)×80 mm (w). Quantity: Abundant. Texture: Semi glossy. Color, mature foliage: Upper Leaf Surface: Green Group 137A. Lower Leaf Surface: Green Group 138A. Color, juvenile foliage: Upper Leaf Surface: Green Group 137A. Lower Leaf Surface: Green Group 138A. Anthocyanin intonation: Present. Location: Intonations of Greyed-Purple Group 183D present on leaflets, petioles, leaf rachis, and stipules.

*Stipules.*—One pair per compound leaf. Size: Variable. 10 mm (l)–18 mm (w). Stipule color: Green Group 138A. Presence of stipitate glands: Present on margins. Margins: Bearded. With undulations. Shape: Broad at base, narrowing at the center, with two spreading tips at the apex. Base is curved inwards at point of attachment. Apex shape pointed, with two separate points at the distal end.

*Petiole.*—Length: 5 mm. Diameter: 1.0–1.5 mm. Petiole color: Green Group 137A. Intonations of Greyed-Purple Group 183D along the margins. Prickles: A few small prickles underneath. Stipitate glands: Limited numbers of stipitate glands on margins.

*Petiole Rachis.*—Length: 8–10 mm. Diameter 1.0–1.5 mm. Color: Green Group 137A. Intonations of Greyed-Purple Group 183D present on margins of juvenile tissue. Margins: Smooth. Prickles: Lacking. Stipitate glands: Limited numbers of stipitate glands on margins.

*Leaflets.*—Size: Average size of the terminal leaflet is 45 mm (l)×30 mm (w). Leaflet shape: Ovate. Base: Obtuse. Apex: Acute. Margins: Serrated. Texture: Leathery. Venation: Pinnate. Color, upper side: Green Group 138A. Color, lower surface: Green Group 138A.

Hips/Seed formation: None observed.

Winter hardiness: To date, the variety has been grown successfully in Zone 5.

Disease resistance: Above average resistance to powdery mildew, blackspot, and rust diseases under normal growing conditions.

I claim:

1. A new and distinct variety of climbing rose plant characterized by the following combination of characteristics:

(a) forms attractive, long lasting pink flowers;

(b) exhibits climbing growth habit;

(c) propagates well using traditional methods, and;

(d) exhibits very good resistance to disease under normal growing conditions; substantially as herein illustrated and described.

* * * * *

'KORcentex'

'KORcentex'